United States Patent
Haller et al.

(10) Patent No.: US 9,198,569 B2
(45) Date of Patent: Dec. 1, 2015

(54) SCOPE DOCK WITH FLUID RESERVOIR

(75) Inventors: Frederick B. Haller, Winston-Salem, NC (US); Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1867 days.

(21) Appl. No.: 11/605,796

(22) Filed: Nov. 29, 2006

(65) Prior Publication Data

US 2007/0142702 A1      Jun. 21, 2007

Related U.S. Application Data

(60) Provisional application No. 60/740,715, filed on Nov. 30, 2005.

(51) Int. Cl.
| | |
|---|---|
| *A61B 1/00* | (2006.01) |
| *A61M 5/32* | (2006.01) |
| *A61M 1/00* | (2006.01) |
| *A61B 1/313* | (2006.01) |
| *A61B 19/00* | (2006.01) |

(52) U.S. Cl.
CPC ............ *A61B 1/313* (2013.01); *A61B 1/00147* (2013.01); *A61B 19/26* (2013.01); *A61B 2019/261* (2013.01)

(58) Field of Classification Search
USPC ......... 600/101, 102, 104, 133, 121, 124, 125, 600/114–116; 605/174, 179; 224/660; 604/160, 174–180, 327–354; 606/193, 606/197
See application file for complete search history.

(56) References Cited

U.S. PATENT DOCUMENTS

| | | | | |
|---|---|---|---|---|
| 3,469,571 | A | * | 9/1969 | Vass .............................. 600/431 |
| 3,977,584 | A | | 8/1976 | Pecoraro ........................... 224/5 |
| 4,265,561 | A | | 5/1981 | Heckele ........................... 403/3 |
| 4,582,508 | A | | 4/1986 | Pavelka ......................... 604/179 |
| 4,854,301 | A | | 8/1989 | Nakajima ......................... 128/4 |
| 4,867,404 | A | | 9/1989 | Harrington et al. ........ 248/231.4 |
| 4,899,730 | A | | 2/1990 | Stennert et al. ................... 128/4 |
| 5,082,111 | A | | 1/1992 | Corbitt, Jr. et al. .......... 206/363 |

(Continued)

FOREIGN PATENT DOCUMENTS

| | | | |
|---|---|---|---|
| JP | 2-13501 | 1/1990 | |
| JP | 2004-086208 | 3/2004 | ............. G02B 23/24 |

OTHER PUBLICATIONS

"AEI Hedburg Chest Brace", *Endoscopy Review: The guide to endoscopic products and services*, Jan./Feb. 1986, p. 10, vol. III, No. 1.

(Continued)

*Primary Examiner* — Ryan Henderson
(74) *Attorney, Agent, or Firm* — Brinks Gilson & Lione

(57) ABSTRACT

A medical device for allowing a physician to unhand a scope or other instruments while maintaining control of the scope or other instruments during a medical procedure. The medical device includes at least one dock and a harness for attaching the dock to the physician's body. The harness can be adjustable, or sized to fit a specific physician. During a procedure, a physician outfitted with the medical device can place a scope and/or other instrument in the dock(s). Once the scope and/or other instrument is placed in the dock(s), the physicians hands are free to perform other procedures, while the physician continually controls the relative position of the scope with respect to the physician or the patient.

26 Claims, 9 Drawing Sheets

(56) References Cited

U.S. PATENT DOCUMENTS

| | | | | |
|---|---|---|---|---|
| 5,137,519 A * | 8/1992 | Littrell et al. | | 604/174 |
| D335,925 S | 5/1993 | Newman | | D24/128 |
| 5,224,680 A | 7/1993 | Greenstein et al. | | 248/316.4 |
| 5,230,622 A | 7/1993 | Brossoit | | 433/31 |
| 5,363,860 A * | 11/1994 | Nakao et al. | | 600/573 |
| 5,441,042 A | 8/1995 | Putman | | 601/109 |
| 5,540,649 A | 7/1996 | Bonnell et al. | | 600/114 |
| 5,571,072 A | 11/1996 | Kronner | | 600/102 |
| 5,755,255 A * | 5/1998 | Iwabuchi | | 137/341 |
| 5,779,623 A | 7/1998 | Bonnell | | 600/114 |
| 5,810,712 A | 9/1998 | Dunn | | 600/114 |
| 5,820,623 A | 10/1998 | Ng | | 606/1 |
| 5,957,423 A | 9/1999 | Kronner | | 248/278.1 |
| 5,993,579 A * | 11/1999 | Farquhar et al. | | 156/47 |
| 6,142,931 A * | 11/2000 | Kaji | | 600/114 |
| 6,145,169 A | 11/2000 | Terzuola et al. | | 24/170 |
| 6,224,571 B1 * | 5/2001 | Bierman | | 604/174 |
| 6,296,164 B1 | 10/2001 | Russo | | 224/602 |
| 6,308,875 B1 | 10/2001 | Almo | | 224/660 |
| 6,461,319 B1 | 10/2002 | Ekey | | 602/62 |
| 6,461,372 B1 | 10/2002 | Jensen et al. | | 606/205 |
| 6,503,192 B1 * | 1/2003 | Ouchi | | 600/114 |
| 6,569,084 B1 | 5/2003 | Mizuno et al. | | 600/102 |
| 6,579,268 B1 | 6/2003 | Loining | | 604/174 |
| 6,712,757 B2 | 3/2004 | Becker et al. | | 600/121 |
| 6,790,201 B2 | 9/2004 | Meyer | | 604/345 |
| 6,971,987 B1 * | 12/2005 | Chung | | 600/102 |
| 2001/0052532 A1 | 12/2001 | Perez et al. | | 224/575 |
| 2002/0103418 A1 | 8/2002 | Maeda et al. | | 600/132 |
| 2003/0102344 A1 | 6/2003 | Godshaw et al. | | 224/605 |
| 2004/0133075 A1 | 7/2004 | Motoki et al. | | 600/131 |

OTHER PUBLICATIONS

Office Action Dated Jun. 17, 2015 from corresponding European Application No. 05 749 813.1, 7p.

* cited by examiner

SCOPE DOCK WITH FLUID RESERVOIR

RELATED APPLICATION

This application claims the benefit of priority from U.S. Provisional Application No. 60/740,715, filed Nov. 30, 2005, and entitled "Scope Dock With Fluid Reservoir", the contents of which is incorporated herein by reference.

TECHNICAL FIELD

This disclosure relates to a medical device for docking an endoscope.

BACKGROUND

Modern, non-invasive surgical procedures often require the use of an endoscope. Endoscopes are thin, tube-like devices used to visualize human anatomies such as the gastrointestinal tract. During endoscopic procedures, a physician manually grips a proximal end of the endoscope. Additionally, in the course of most endoscopic procedures, physicians manipulate and maneuver the endoscope in a variety of ways to rotate, adjust, or torque the endoscope.

At some stage in an endoscopic procedure, a physician may need to release the endoscope, for example, to perform an ancillary procedure or write notes. To do this, the physician carefully hands the endoscope to a nurse or places the scope in a stationary docking station. Docking stations are stands for receiving and holding an endoscope. Docking stations are typically affixed to a stationary point, such as a ceiling, wall, or floor. Other docking stations can be part of or affixed to a chair, a bed, or a table.

Both handing the endoscope to a nurse and docking the endoscope in a traditional docking station present significant drawbacks. First, whether the physician hands the endoscope to a nurse or docks it in a traditional docking station, the physician is disconnected from the patient during the procedure—even though the endoscope is still engaged in the patient's body. That is, the physician loses direct control of the endoscope. Second, presently available docking stations have very limited functionality. As a result, conventional docking stations are only suited for stationary hanging or gripping an endoscope that is not in use.

BRIEF SUMMARY

Accordingly, it is an object of the present invention to provide a medical device having features that resolve or improve upon one or more of the above-described drawbacks.

The invention is defined by the following claims, and nothing in this section should be taken as a limitation on those claims.

One aspect of the present invention provides a scope dock including a harness and a main body. The harness allows the scope dock to be attached to an operator, and the main body may include a scope holder which receives a scope. The harness may be a shoulder harness, midsection harness, or any other type of harness. The scope holder may hold the scope directly or through the use of other devices situated on the scope or the scope holder.

In another aspect of the present invention, the scope dock comprises a removable scope bearing sleeve which receives a scope. The scope bearing sleeve may include a device clip for holding an elongate device. The scope bearing sleeve may also include a fluid reservoir for collecting any fluid that be expelled from the scope or elongate device.

This invention also provides a method for using a scope dock. The method comprises a step of attaching a-scope dock to an operator and a step of docking a scope in the scope dock. A catheter may be inserted into the scope as another step or another medical procedure may be performed.

Other embodiments are disclosed, and each can be used alone or in combination with another.

DETAILED DESCRIPTION OF THE INVENTION

Figure 1:
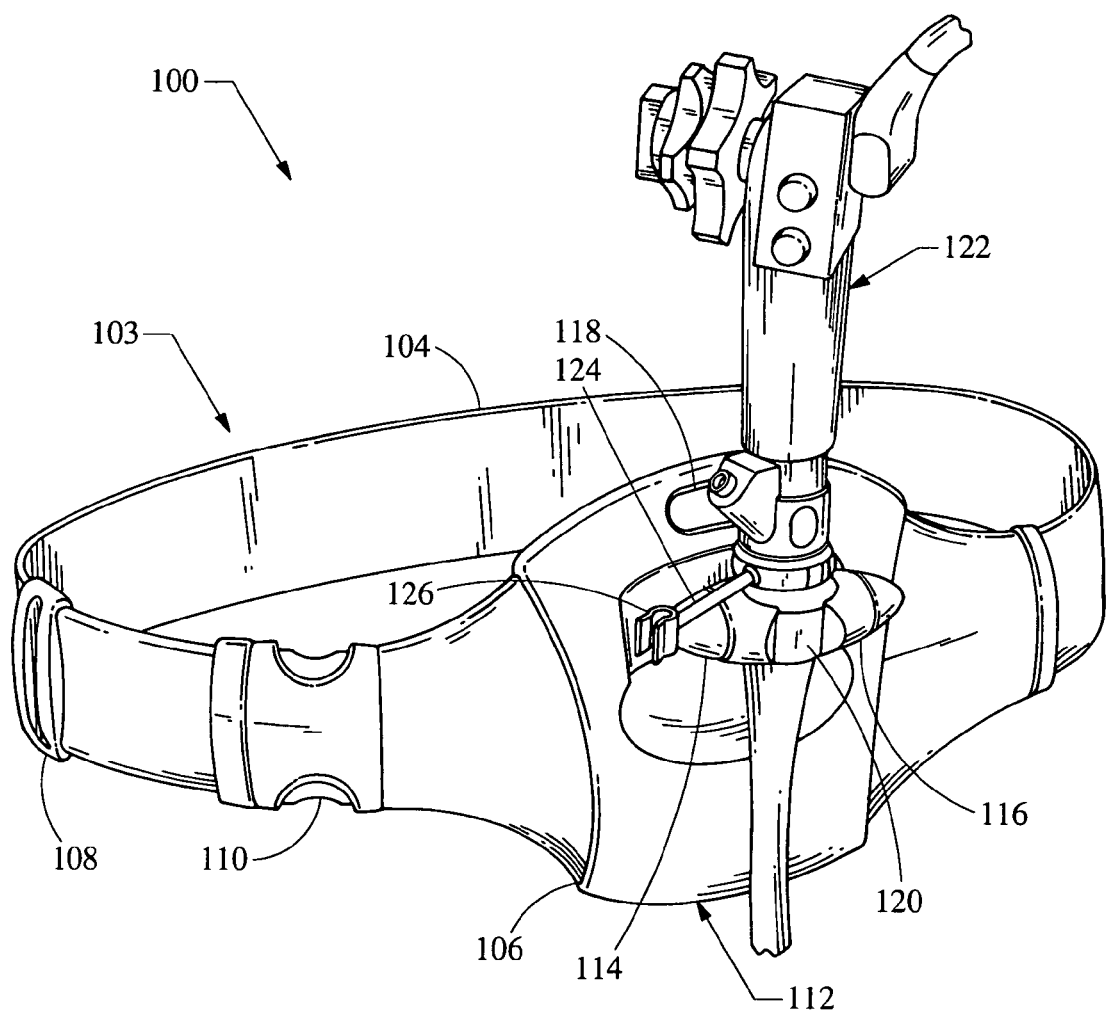
FIG. 1 illustrates a perspective view of a scope dock having a hub.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

Turning now to FIG. 1, that figure discloses a scope dock 100 and a hub 102. The scope dock 100 includes a harness 103 comprising a belt 104, a waist adjustment 108 to adjust the length of the belt, and a belt buckle 110 to allow the belt to be buckled and unbuckled in order to put on and take off the scope dock 100. The belt 104 is connected to a main body 106. The main body broadens into a central portion 112 which includes a scope holder 114 and a scope pivot 116. The scope pivot 116 is allowed to pivot by the scope holder 114. The scope holder 114 may optionally maintain the scope pivot 116 at various pivot positions from the vertical, such as at 0°, 15°, and 30° from the vertical. The central portion also includes a release button 118 which releases the scope holder from an inactive position, where it is flush with the central portion, to an active position, where it is approximately perpendicular to the central portion. When the scope holder is in the active position, it may be locked into place, such that the scope holder may not be unlocked or moved until the release button is again pressed.

A scope bearing sleeve 120 slides onto a scope 122, such as an endoscope. The scope bearing sleeve is optionally in a friction fit relationship with the scope, which may hold the two together in such a way that they do not move. At the same time, the scope bearing sleeve and the scope pivot are arranged such that the scope bearing sleeve is able to rotate coaxially within the scope pivot. The exemplary scope pivot shown here includes a chamfered out portion that allows the scope bearing sleeve to sit in the scope pivot. Additionally, at least one optional device hub 124 may be clipped onto the scope bearing sleeve, and the device hub may have a device clip 126 on its end. The device clip 126 may clip onto a variety of medical devices, such as catheters or other devices used with the scope.

Furthermore, the main body in this exemplary embodiment may comprise a semi-rigid over-molding, which is rubberized. Such a material may allow the main body to comfortably flow around the mid-section of the doctor while he is wearing the scope dock. Though a semi-rigid material is shown here, any variety of flexible or rigid or semi-rigid materials may be used to manufacture the main body of the scope dock.

Additionally, the belt 104 may be made of nylon braid or any suitable material, such as rubber, leather, plastic, natural or synthetic threads, or any other material that may be used to make a belt. The waist adjustment may be a single clip—or any other suitable clip or device—that allows the belt to be lengthened or shortened depending on the size of the mid-section of a doctor and the desired level of tightness about the doctor. Though the exemplary waist adjustment shown in FIG. 1 is separate of the belt buckle, it may also be integral with the belt buckle. The belt buckle shown in FIG. 1 is a parachute type belt buckle having two finger grips that may be pressed together to unbuckle the belt. Even though a parachute type belt buckle is shown here, any type of clip arrangement, belt buckle, hook and loop fastener, or other suitable device may be used to secure the belt. Moreover, though the exemplary scope dock of FIG. 1 uses a belt as a harness to secure the scope dock, a wide variety of harnesses may be used to secure the scope dock to the doctor, such as shoulder harnesses, neck harnesses, leg harnesses, or other types of harnesses.

The scope bearing sleeve may be made of a hardened plastic, but the sleeve may also be made of metal, rubber, a harder or softer plastic, or any other suitable material. Alternatively, the scope bearing sleeve may be disposable after one use or reusable for any number of uses. The scope bearing sleeve may also be integral with the scope or included with the scope at the time of scope purchase. Similarly, the device hub is made of a hardened plastic or any suitable material. The device hub may be disposable after one use or reusable for a number of procedures or a period of time. The device hub, as well, may be rotatable about the scope bearing sleeve, and the hub and sleeve may share a frictional or other type of fit. If a frictional fit is used, the fit may be such that the device hub and the scope bearing sleeve are stably maintained by the fit in a particular position relative to one another. At the same time, the frictional fit may optionally allow the hub and sleeve to be moved relative to one another by the application of a certain amount of force, such as a light or medium pressing of the hub by the doctor or nurse. Further, the clip of the device hub may itself be coaxially rotated, depending upon the needs of the doctor. This coaxial rotation is an optional feature of the device hub. The exemplary scope bearing sleeve of FIG. 1 is—but is not necessarily—cut to fit around the access port of the scope, and this may increase the stability of the fit such that the scope bearing sleeve does not rotate in relation to the scope while in use. Optionally, the scope bearing sleeve may be different in configuration and design based upon the brand and type of scope used in order to fit the respective scope.

Figure 9:
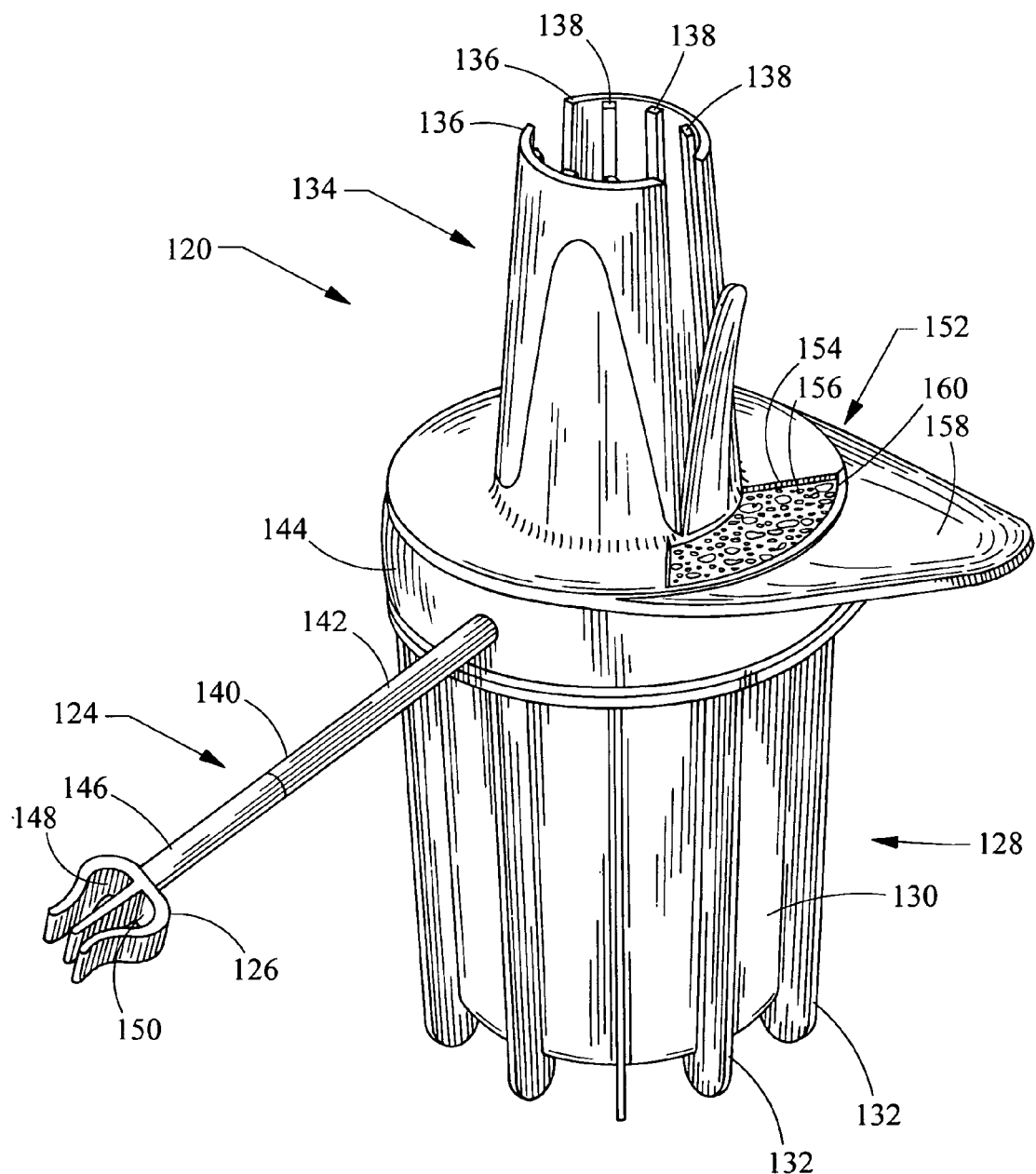
FIG. 9 illustrates a perspective view of a scope bearing sleeve for use with a scope dock.

An alternative embodiment of the scope bearing sleeve 120 is illustrated in FIG. 9. In this particular embodiment, the scope bearing sleeve 120 comprises a scope dock engagement portion 128 that is configured to slidably engage the scope holder 114 of the scope dock 100 (see FIG. 1). The scope dock engagement portion 128 comprises a tubular body 130 with a plurality of longitudinally oriented engagement ribs 132 spaced circumferentially about the exterior thereof. The engagement ribs 132 comprise a flexible or compliant material such as rubber that frictionally engages with the interior surface of the scope holder 114. This frictional arrangement prevents or inhibits accidental, unintended or inadvertent movement or removal of the scope bearing sleeve 120 from the scope holder 114. The engagement ribs 132 also provide a damping mechanism to eliminate or reduce the transmission of vibrations or small movements between the endoscope 122 and the user.

The scope bearing sleeve 120 of FIG. 9 further comprises a scope engagement portion 134 that that is configured to slidably engage a scope 122 (see FIG. 1). The scope engagement portion 134 comprises a pair of opposed semi-circular body portions 136 with a plurality of longitudinally oriented engagement ribs 138 spaced circumferentially about the interior surface thereof. The open space between the semi-circular body portions 136 is generally configured to accommodate the working channel port or other components projecting from the side of the scope 122. The engagement ribs 138 comprise a flexible or compliant material such as rubber that frictionally engages with the exterior surface of the scope 120. This frictional arrangement prevents or inhibits accidental, unintended or inadvertent movement or removal of the scope 122 from the scope bearing sleeve 120.

The bearing sleeve 120 of FIG. 9 further comprises a device hub 124 that is rotatably and removably attached to a central portion thereof. In particular, the device hub 124 includes a stem 140 having a proximal portion 142 that is affixed to a C-shaped clip 144 that is removably disposed in a recess in the central portion of the bearing sleeve 120. This arrangement allows the device hub 124 to rotate about the longitudinal axis of the bearing sleeve 120, as well as to be completely removed therefrom. The distal portion 146 of the stem 140 is attached to a device clip 126 that is configured to engage and hold stationary one or more elongate devices, e.g., a catheter or a wire guide (not shown). The distal portion 146 is rotatably attached to the proximal portion 142 so as to permit rotation of the device clip 126 to axially rotate relative to the stem 140. In the particular device clip 126 illustrated, the device clip 126 includes a first clip portion 148 having a first size and a second clip portion 150 having a second size, wherein the second size is larger than the first size so as to allow the device clip 126 to engage a variety of differently sized elongate devices.

The bearing sleeve 120 of FIG. 9 further comprises a fluid reservoir 152 for collecting fluids that may be expelled from the scope 122 (see FIG. 1) during the medical procedure. For example, fluids may be expelled from the scope's working channel or from elongate devices extending through the scope's working channel. This fluid tends to drip down the exterior surface of the endoscope, thereby contaminating or otherwise interfering with the scope or other devices. The fluid also presents a contamination, germ or disease risk to the physician and assistants during the medical procedure. The fluid reservoir 152 comprises a cavity 154 disposed within the central portion of the scope bearing sleeve 120. The cavity 154 is preferably large enough to hold the volume of fluid that may be anticipated will leak from the scope or other devices. The cavity 154 may also include a sponge 156 to help prevent any fluid collected in the cavity 154 from leaking out therefrom, and to facilitate removal of the fluid from the cavity 154 after completion of the medical procedure. The fluid reservoir 152 further comprises a drip catcher 158 that projects outwardly from the scope bearing sleeve 120 and is sized and oriented so as to catch fluid leaking from the scope 120 when the scope 120 and scope dock 100 are in a variety of positions and orientations. The drip catcher 158 is angled or sloped so as to direct fluid dripping onto the upper surface thereof towards the opening 160 of the cavity 154. The drip catcher 158 also comprises a concaved upper surface to likewise direct fluid dripping onto the upper surface thereof towards the opening 160 of the cavity 154.

Figure 2:
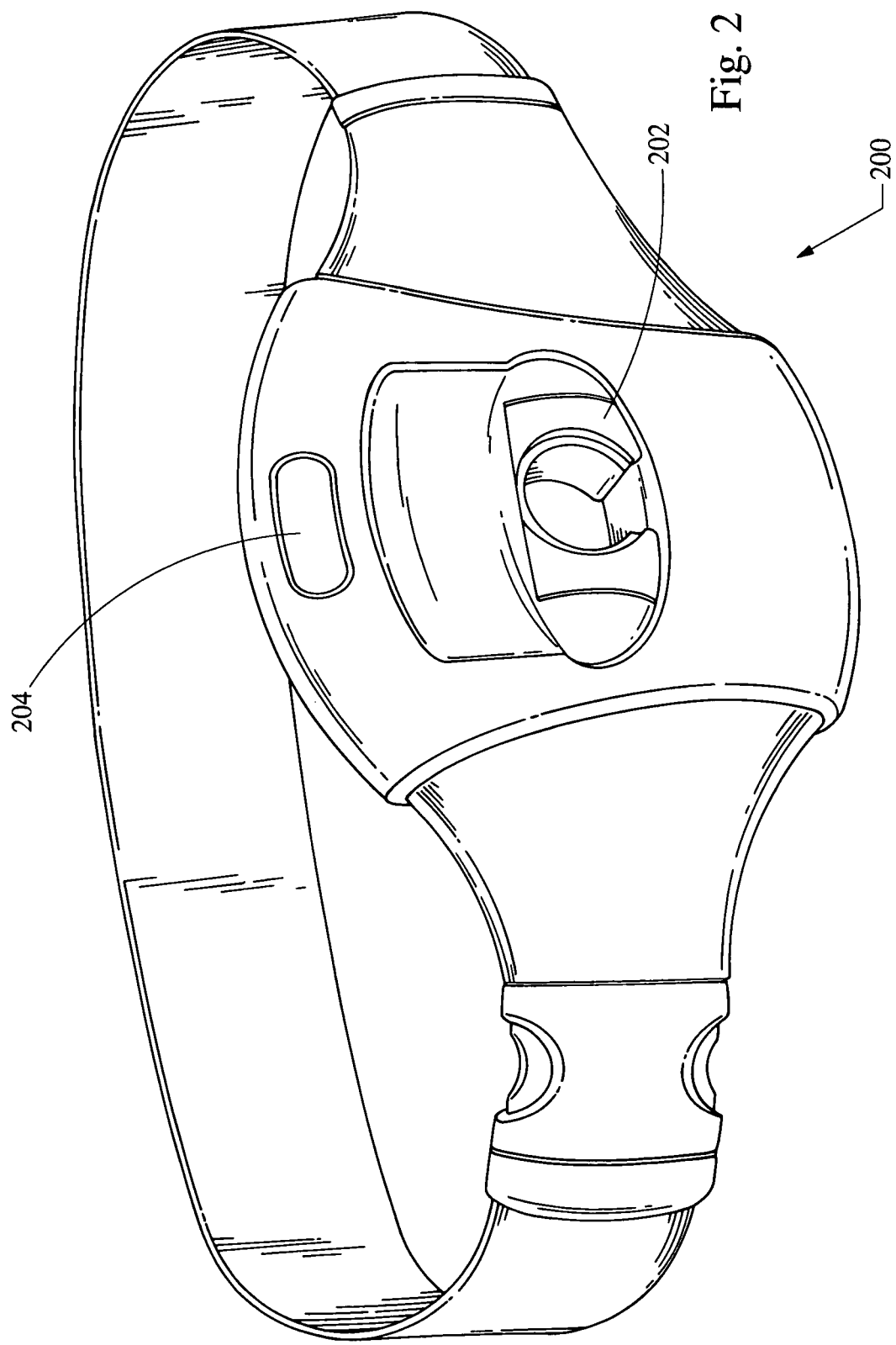
FIG. 2 illustrates a perspective view of a scope in a retracted position.

Turning now to FIG. 2, that figure discloses a scope dock 200 similar to the one shown in FIG. 1. The scope dock 200 has a scope holder 202 in an inactive retracted position. When a scope (not shown) is not needed at a particular time during a procedure or before a procedure, the doctor may remove the scope from the scope holder, and he may retract the scope holder. The scope holder maintains a scope pivot, in a similar way as the scope holder 114 maintains scope pivot 116 of FIG. 1.

Because of its low profile, the exemplary scope dock 200 need not be removed when not in active use. In fact, the scope dock 200 itself may assist a doctor in bearing the weight of a lead apron (not shown), which the doctor may wear during a medical procedure. As noted earlier, in order to activate the scope holder 202, a doctor or his assistant may press the release button 204 to allow the scope holder 202 to rotate to a locked position approximately perpendicular to a main body of the scope dock 200.

Figure 3:
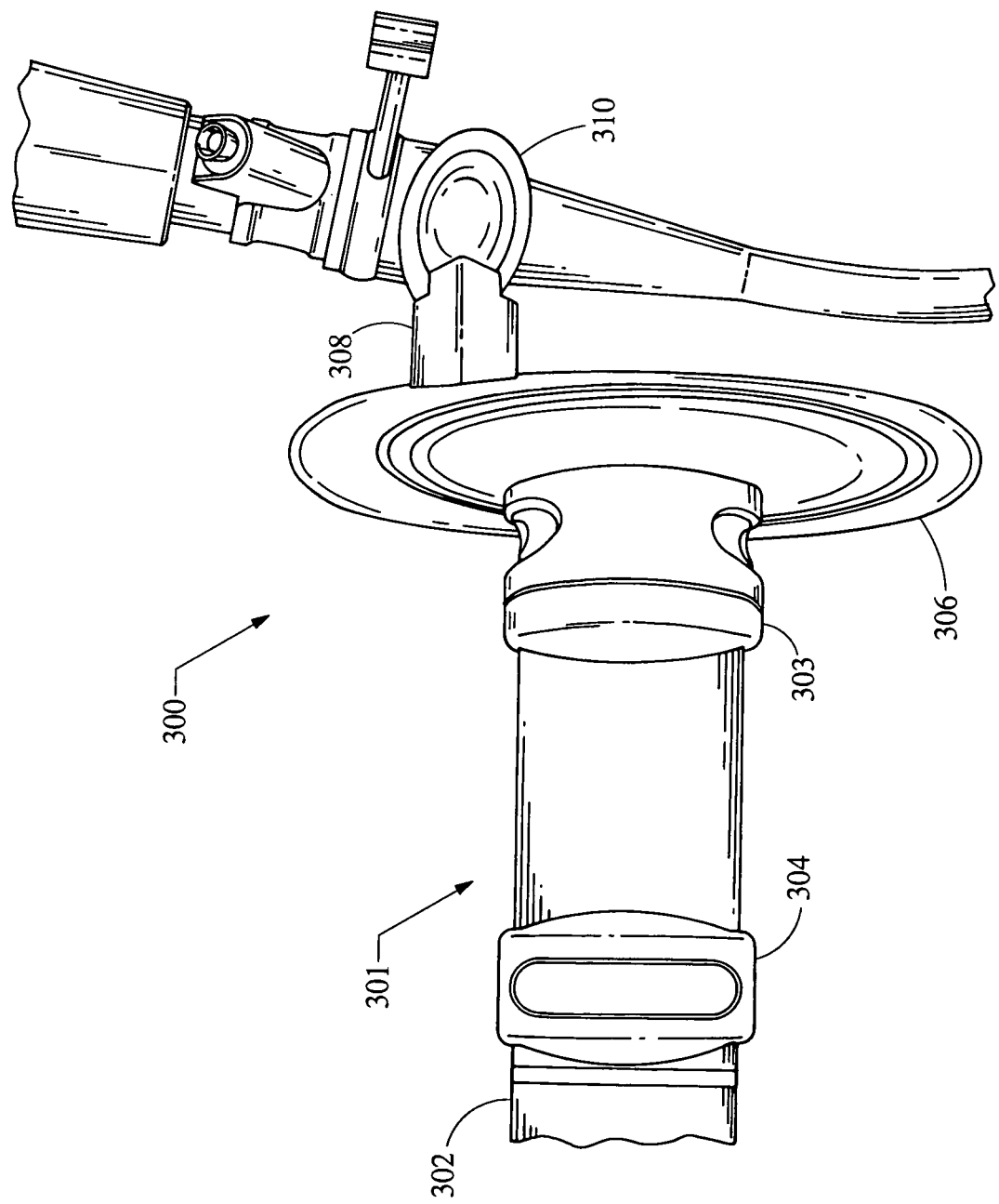
FIG. 3 illustrates a side view of an endoscope situated in a scope dock.

Turning now to FIG. 3, that figure discloses a side view of scope dock 300, which is similar to the scope docks 100, 200 shown in FIGS. 1 and 2. The scope dock 300 includes a harness 301, comprising a belt 302, a buckle 303, and a waist adjustment 304, connected to a main body 306. Extending from the main body 306 is a scope holder 308 which maintains a scope pivot 310. The scope pivot 310 is shown at a 15° rotation from the vertical, and a scope and scope bearing sleeve are seated in the scope pivot. The scope bearing sleeve also has a device hub attached to it. In the exemplary embodiment of FIG. 3, the scope pivot may be adjusted to a 0°, 15°, or 30° rotation from the vertical. Similar to the example in FIG. 1, the scope bearing sleeve may rotate within the scope pivot, and the device hub may rotate about the scope bearing sleeve.

Figure 4:
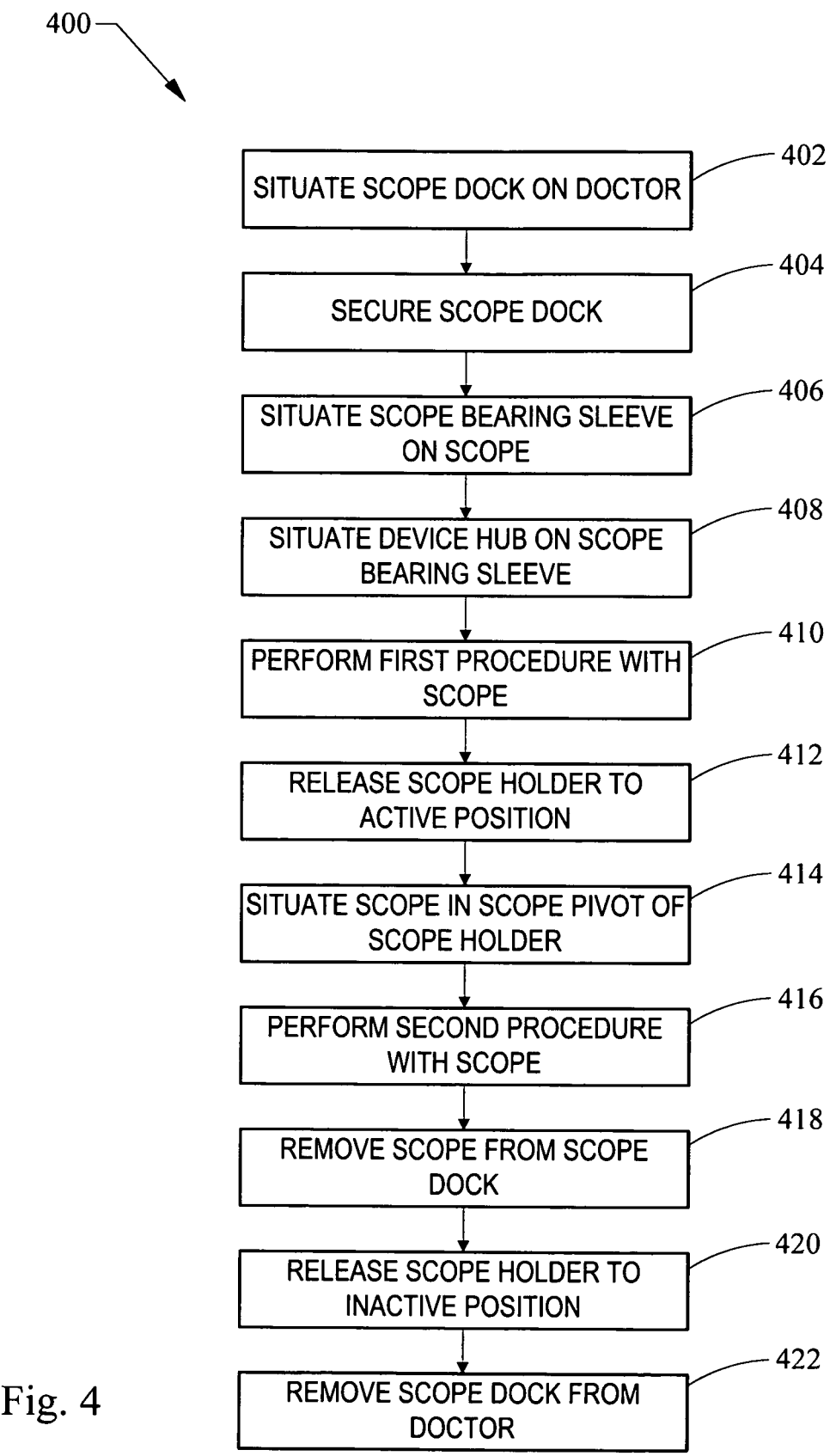
FIG. 4 illustrates a flow-chart of exemplary steps for using a scope dock.

Turning now to FIG. 4, that figure discloses an exemplary method 400 of performing a medical procedure using a scope dock similar to the ones disclosed in FIGS. 1-3. Though the method 400 steps are shown in an order for the sake of the present example, some of them are optional, and many of them may be performed in a different order than that presented in this example. In a procedure that may involve the use of radioactive substances, a doctor may wear a lead apron or other protective clothing over standard hospital clothing. Often, this clothing extends across the region of the body upon which the scope dock will be situated, and so, the protective clothing may be in place prior to performing method 400.

In step 402, the scope dock is situated on the doctor. The scope dock can be fastened around the doctor's midsection (FIGS. 1-3), placing a shoulder harness over his head and onto his shoulders, placing a neck harness around his neck, or situating the scope dock in any other way on the doctor. Then, in step 404, the scope dock is secured to the doctor by buckling a belt buckle, fastening a Velcro hook and loop fastener, or securing the scope dock in any other way. In some instances, the steps 402, 404 of situating and securing may be performed as one action or the step 402 of situating may also provide the securing onto the doctor—such as in the case of a shoulder harness that may have adjustment devices but no additional securing devices.

Step 406 comprises situating a scope bearing sleeve onto the scope. This particular step 406 is optional, depending on the scope dock in use, and may be performed at a variety of times—before the doctor even arrives in the procedure room, before the procedure has begun, just prior to use of the scope, or any appropriate time. Situating a device hub onto the scope bearing sleeve is step 408. This step 408 is also optional, and in an alternate embodiment, the device hub may be situated onto the main body of the scope dock or onto the scope itself. This step 408 may also be performed at a any appropriate time before or during a procedure, and any number of device hubs may be situated, depending on the needs of the doctor.

The exemplary method 400 shows an optional feature of the scope dock system in step 410. In this exemplary step 410, a doctor performs a first procedure with the scope, after the step 402 of situating the scope dock on the doctor and before the step 414 of situating the scope in the scope dock. Though shown in this sequence for the sake of example, these steps may be performed in any order and in a variety of ways. This first procedure may be any kind of procedure, such as inserting the scope into the patient's mouth or performing a test on the scope itself.

Then, the doctor or nurse releases a scope holder on the scope dock to an active position in step 412. This step 412 of releasing may involve the pressing of a release button—as shown on the exemplary scope docks of FIGS. 1 and 2—manipulating the scope holder to an active position manually, or some other releasing. The releasing of step 412 is optional, as some scope docks may not have a releasing functionality, or the releasing may be performed at a different time before or during a procedure. Next, in step 414, the doctor or nurse may situate the scope and scope bearing sleeve into the scope pivot of the scope holder by moving the scope laterally through the open portion of the scope holder and then lowering the scope and scope bearing sleeve into the scope pivot of the scope holder. The optional scope pivot featured in FIGS. 1-3 may allow coaxial rotation of the scope while situated in the scope dock, and the scope pivot may allow for the scope to be situated at different angles in relation to the scope dock or the vertical plane. As noted above in FIGS. 1-3, the various features of the scope pivot are optional, as is the scope pivot itself. In some exemplary scope docks, the scope holder itself may hold the scope without using a scope pivot, and in some exemplary scope docks, the scope may be situated on the scope dock without using a specific scope holder portion.

In exemplary step 416, the doctor performs a second procedure with the scope situated on the scope dock. This second procedure may be any kind of procedure, such as a inserting a catheter or wire guide into an access port of the scope, viewing the inside of the patient on a monitor, performing a cannulation using a catheter, shooting fluoroscopy inside a patient, writing a note on the condition of the patient, or any other procedure.

In step 418, the doctor or nurse removes the scope from the scope dock. In the exemplary scope dock of FIGS. 1-3, this may involve removing the scope bearing sleeve from the scope pivot. As noted earlier, this step 418 may be performed at a variety of times and in a variety of ways during a scope procedure. After the scope is removed from the scope dock, the scope holder may be released to the inactive position in step 420. In the exemplary FIGS. 1-3, this may involve pressing the release button to release the scope holder and then manually pressing the scope holder down until it is in an inactive position. Even so, the scope holder may be implemented in a variety of ways, such as being fixed in position; automatically moving from active to inactive position at the press of a button; released by using a lever, switch, or other mechanism; or in some other way.

Finally, in step 422, the scope dock is removed from the doctor. This may involve unbuckling a belt buckle, removing a harness, or other way of releasing the scope dock. The scope dock of exemplary FIGS. 1-3 may be unbuckled by either the doctor or nurse and set aside for sanitization and the next procedure. Additionally, in step 424, the scope bearing sleeve may be removed from the scope. After removal, the scope bearing sleeve may be thrown away, if it is a disposable sleeve, or set aside for sanitization and the next procedure, if it is a reusable sleeve. As noted above, some scope docks do not work in conjunction with a scope bearing sleeve, and therefore, in these instances, step 424 and other steps involving the sleeve would be unnecessary.

In use, a doctor may buckle the scope dock around himself prior to a procedure. Then, the scope bearing sleeve may be slid onto the scope and brought into a friction fit with it. At the appropriate point in the procedure, the scope bearing sleeve and the scope may be seated in the scope bearing hub of the scope dock. In this way, the doctor is able to have an extra free hand to write notes, to grab on to a catheter, or to perform another desired portion of the medical procedure. During a procedure, the doctor may insert a catheter into the endoscope, and after this, he may wish to dock the handle of the catheter into the device clip of the device hub. In this way, he does not need to support the other end of the catheter or worry about where the other end of the catheter is, as it would be immediately in front of him at a convenient position for hand activation. Additionally, the doctor may rotate the device hub and the device clip in order to position a handle or other end of a catheter in whatever position he desires. While in the device hub, the catheter handle may be manipulated without having to maintain the entire end of the catheter independently.

Figure 5:
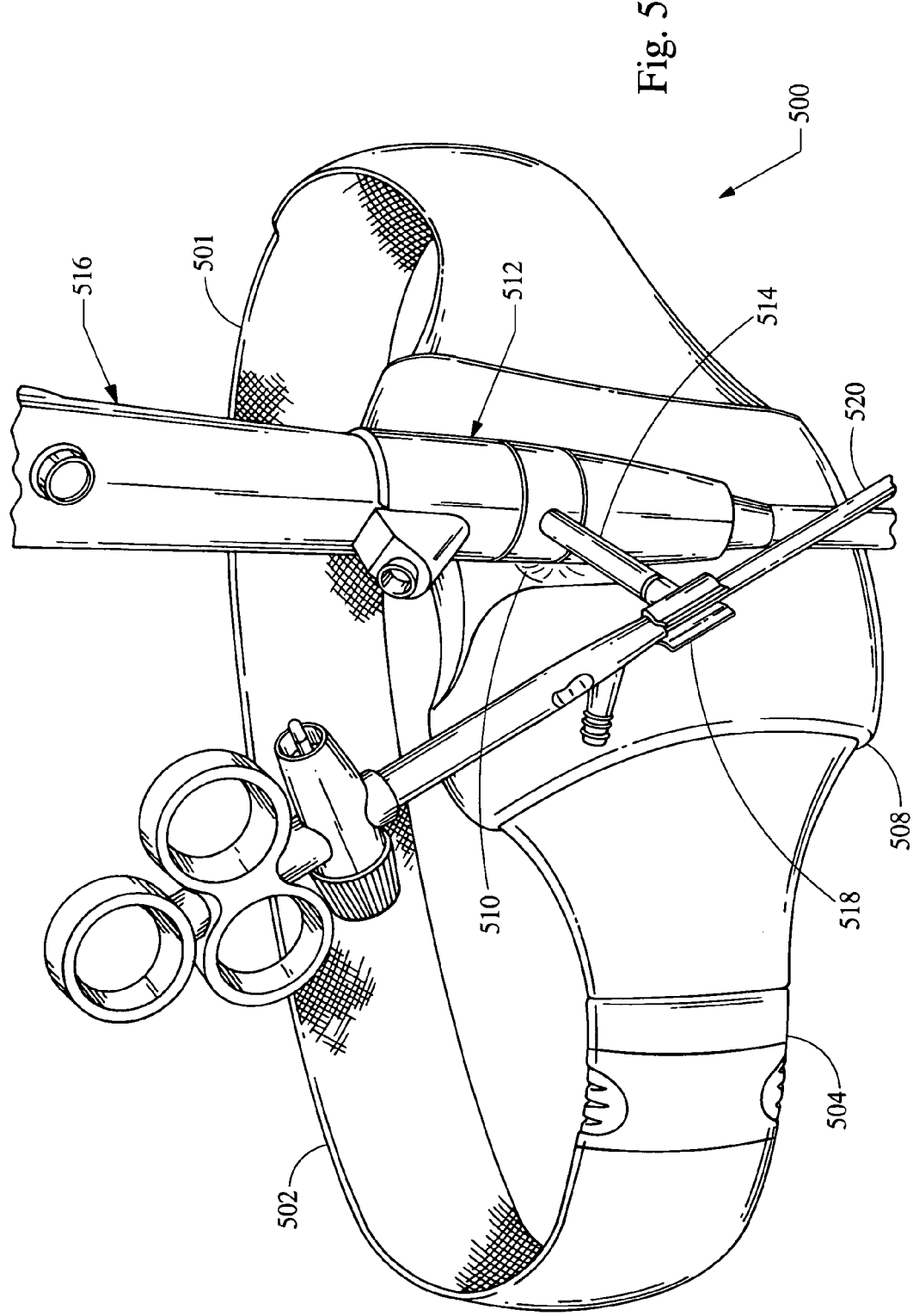
FIG. 5 illustrates a perspective view of a scope dock having an integral device hub.

Turning now to FIG. 5, that figure discloses an exemplary embodiment of a scope dock 500. The scope dock 500 includes a harness 501 comprising a belt 502, a belt buckle 504, and waist adjustment 506. The belt 502 is attached to a main body 508 which has a scope receiving hub 510. A scope bearing sleeve 512 is seated in the scope receiving hub 510, and a device hub 514 is integral with the scope bearing sleeve 512. The scope bearing sleeve 512 is friction fit around a scope 516, preferably prior to commencing a medical procedure involving the scope 516. In this embodiment, the device hub 514 is rotatable within the scope bearing sleeve 512, and the device hub 514 has an independently rotatable device clip 518 at its end. The device clip 518 is able to receive a variety of devices and is shown here attached to the wrapping portion of a catheter 520. The catheter 520 has a handle and multiple ports. The handle may be actuated and the ports accessed while the catheter 520 is situated in the device clip 518.

Figure 6:
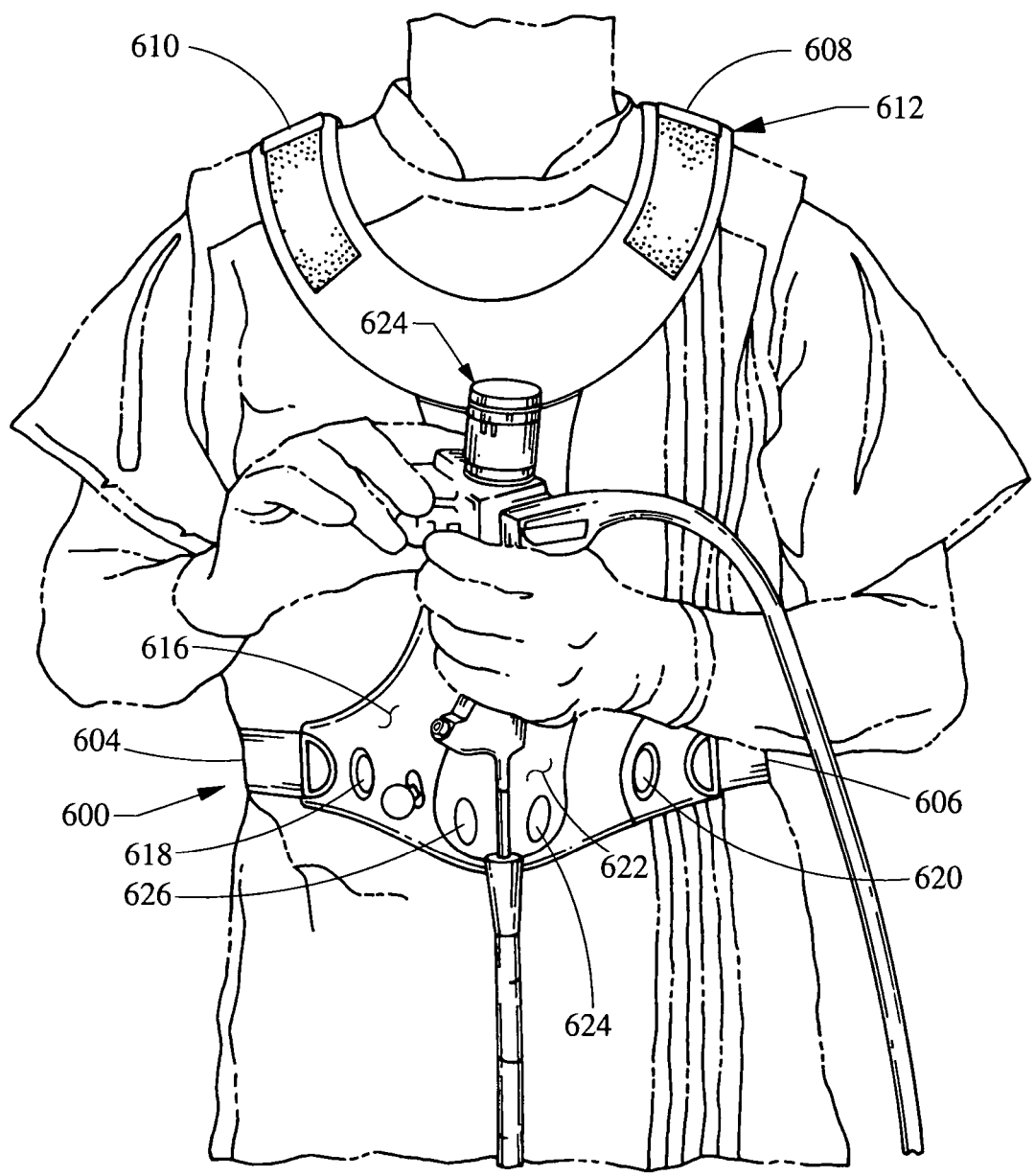
FIG. 6 illustrates a front view of a user wearing a scope dock configured with a chest support and a waist support.

Turning now to FIG. 6, that figure discloses an exemplary embodiment of a scope dock 600. The scope dock 600 includes a harness 602 having midsection straps 604, 606, shoulder straps 608, 610, a shoulder support 612, and a back plate 614. The midsection straps 604, 606 connect to a main body 616 by clips (not shown), which may be released by pressing clip release buttons 618, 620, respectively. The operator or his assistant may adjust the straps at the shoulder support 612, belt buckles 616, 618, or back plate 614. A scope bearing hub 622 receives the scope 624. The scope 624 and the scope bearing hub 622 may share a friction fit, as well. The scope bearing hub 622 shown here is a removable ball seated in a socket joint. The scope bearing hub 622 has opposing finger rests 624, 626 that may be squeezed together to release the scope bearing hub 622 from the socket joint and, thereby, from the main body 616. This allows simple removal of the scope bearing hub 622 from main body 616.

Figure 7:
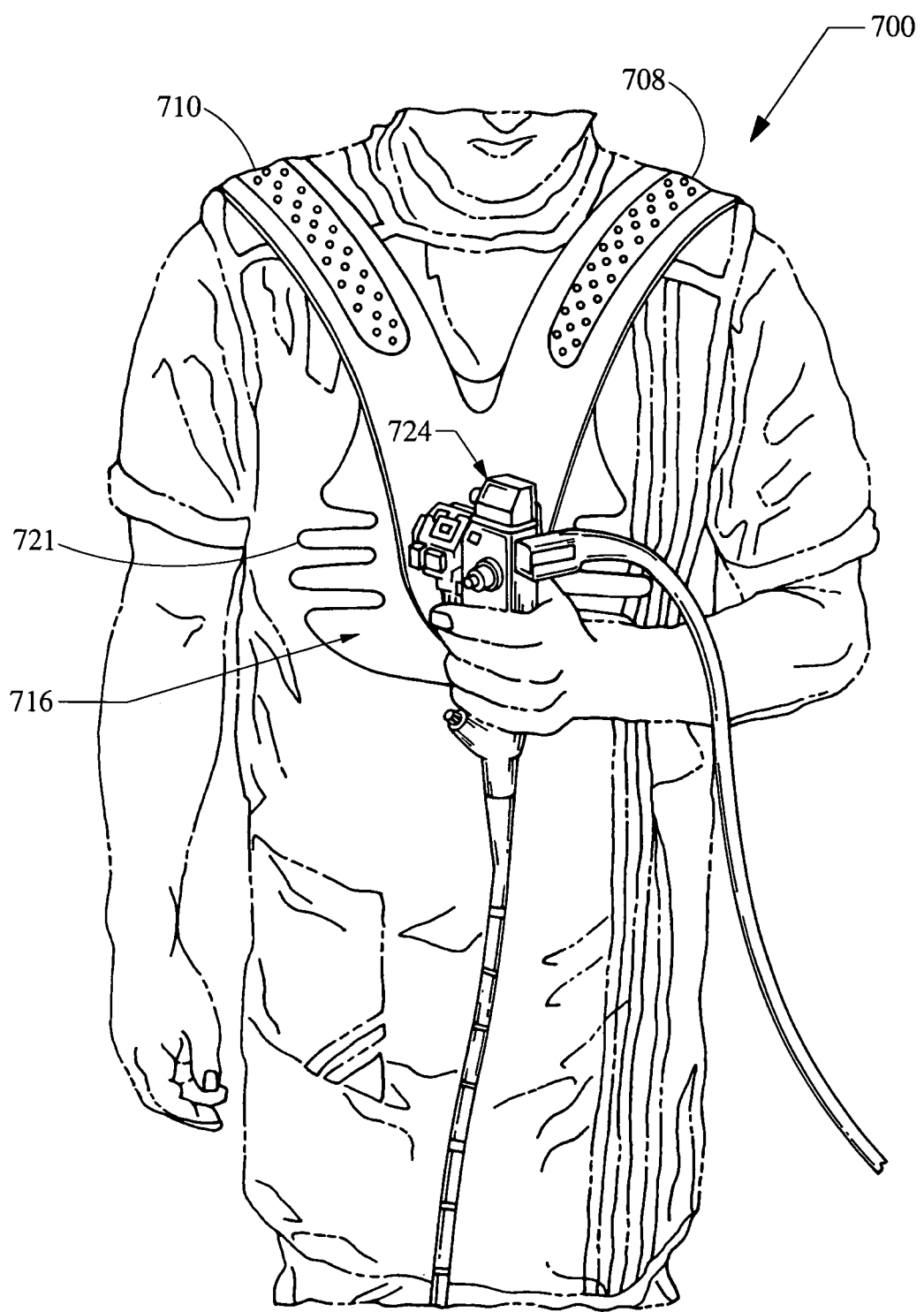
FIG. 7 illustrates a front view of a user wearing a scope dock configured with a chest support.

FIG. 7 illustrates an exemplary embodiment of scope dock 700, which is configured as a chest support. Scope dock 700 includes a harness having chest straps 708 and 710 that are integral to a main body 716. The main body is provided with a docking mechanism as described above regarding the previous embodiments. That is, the main body is outfitted with a scope receiving hub as detailed in any of the above-described embodiments. The scope receiving hub allows a physician to dock or release the endoscope as needed. As illustrated in FIG. 7, the scope dock 700 includes a widened portion 721. Widened portion 721 is adapted to distribute the weight of the endoscope about the chest of a physician. Widened portion 721 further provides a stable platform for the physician. Of course, scope dock 700 can alternatively be provided with without a widened portion 721.

Figure 8:
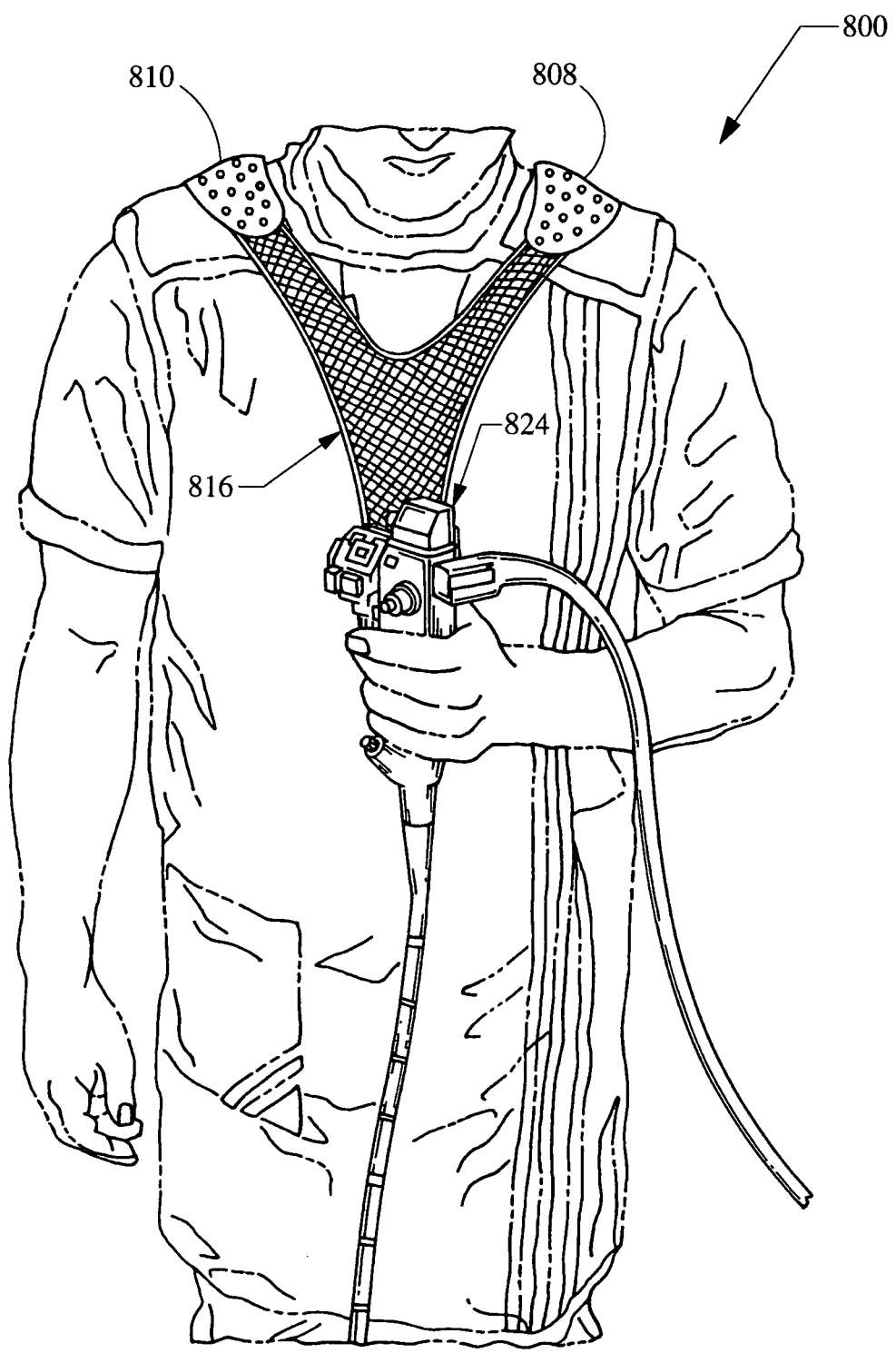
FIG. 8 illustrates a front view of a user wearing a scope dock configured with a neck support.

FIG. 8 illustrates an exemplary embodiment of scope dock 800, which is configured as a neck support. Scope dock 800 is similar to the scope dock shown in FIG. 7. Scope dock 800, however, is adapted to be worn about a physician's neck, rather than the shoulders. For comfort, scope dock 800 can be provided with neck pads 810 and 808. Neck pads 810 and 808 can be formed from a wide variety of widely available cushion materials, such as high density foam. Scope dock 800 further includes a Y-shaped main body 816 having a scope receiving hub as detailed in any of the previously described embodiments. Main body 816 can be formed of a lightweight, durable material, for example, plastic or carbon fiber.

It is to be understood that changes and modifications to the embodiments described above will be apparent to those skilled in the art, and are contemplated. Such changes include varying the configuration of the disclosed harnesses. Alternative harnesses could include strapless harness variations. For example, it will become apparent to one of ordinary skill that a protective garment, a jacket, or a vest could be used as a harness for a scope dock. Indeed, a scope dock could be provided integrally with a protective lead vest. It is therefore intended that the foregoing detailed description be regarded as illustrative rather than limiting, and that it be understood that it is the following claims, including all equivalents, that are intended to define the spirit and scope of this invention.

The invention claimed is:

1. A medical device for use with a scope having a handle and an elongate tubular portion extending from the handle along a longitudinal axis thereof, the medical device comprising:

a central portion configured to be positioned on a user;

a scope holder attached to the central portion, the scope holder having a channel configured to secure the scope, the scope being secured with the longitudinal axis of the elongate tubular portion aligned with a central axis of the scope holder, the scope holder being configured to laterally receive the elongate tubular portion of the scope along a direction transverse to the central axis of the scope holder; and a scope bearing sleeve disposed within the scope holder, the scope bearing sleeve having a fluid reservoir surrounding the scope configured to collect fluid expelled from the scope, the reservoir comprising a partially enclosed cavity having an open top through which the fluid enters the cavity by gravitational forces, the cavity being configured to limit contact by the user with the fluid collected therein, wherein a drip catcher is disposed adjacent to the fluid reservoir for directing the fluid towards the open top and into the cavity of the fluid reservoir, the drip catcher having an upper surface projecting outwardly and upwardly from the open top of the cavity so as to direct by gravitational forces fluid towards the open top.

2. The medical device of claim 1 wherein the channel is defined by a wall having an open portion that is adapted to laterally receive the elongate tubular portion of the scope.

3. The medical device of claim 2 wherein the scope holder is rotatable.

4. The medical device of claim 3 wherein the scope holder is rotatable about a horizontal axis.

5. The medical device of claim 4 wherein the scope holder is rotatable about a vertical axis.

6. The medical device of claim 3 wherein the scope holder is rotatable about a vertical axis.

7. The medical device of claim 2 wherein the central portion comprises a belt configured to be secured to the user.

8. The medical device of claim 7 wherein the belt comprises a buckle for connecting the belt to the central portion.

9. The medical device of claim 2 wherein the central portion comprises a shoulder harness configured to be secured to the user.

10. The medical device of claim 2 wherein the central portion comprises a chest harness configured to be secured to the user.

11. The medical device of claim 2 wherein the central portion comprises a neck harness configured to be secured to the user.

12. The medical device of claim 2 wherein the central portion comprises a protective apron configured to be secured to the user.

13. The medical device of claim 1 wherein the channel is adapted to laterally receive the handle.

14. The medical device of claim 1 wherein the scope bearing sleeve is configured to removably nest in the scope holder.

15. The medical device of claim 14 wherein the cavity of the fluid reservoir is formed in the scope bearing sleeve.

16. The medical device of claim 14 further comprising a hub comprising a clip, the clip being adapted to secure an elongate medical device, the hub being operably connected to the scope bearing sleeve.

17. The medical device of claim 16 further comprising a second clip positioned adjacent the first clip.

18. The medical device of claim 16 further comprising an arm disposed between the scope bearing sleeve and the clip, wherein the arm is rotatable relative to the scope bearing sleeve.

19. The medical device of claim 1 wherein at least a portion of the scope holder is releasably attached to the central portion.

20. The medical device of claim 1 wherein the scope holder is configured to receive one of a catheter, a wire guide, and a scope.

21. The medical device of claim 1 further comprising a ball and socket joint configured to connect the scope holder to the central portion.

22. The medical device of claim 1 wherein the fluid reservoir includes a sponge disposed in the cavity for absorbing the fluid collected therein.

23. The medical device of claim 1 wherein the drip catcher comprises a concaved upper surface configured to direct fluid flow towards a central portion of the open top.

24. The medical device of claim 1 wherein the drip catcher comprises a free edge that is spaced away from both the open top of the reservoir and the scope holder.

25. A medical device for use with a scope having a handle and an elongate tubular portion extending from the handle, the medical device comprising:
  a central portion configured to be positioned on a user;
  a scope holder attached to the central portion, the scope holder having a channel configured to laterally receive and secure the scope;
  a bearing sleeve disposed within the scope holder, the bearing sleeve having a fluid reservoir surrounding the scope configured to collect fluid expelled from the scope, the reservoir comprising a partially enclosed cavity having an open top through which the fluid enters the cavity by gravitational forces, the cavity being configured to limit contact by the user with the fluid collected therein,
  wherein a drip catcher is disposed adjacent to the fluid reservoir for directing the fluid towards the open top and into the cavity of the fluid reservoir, the drip catcher having an upper surface projecting outwardly and upwardly from the open top of the cavity so as to direct by gravitational forces fluid towards the open top,
  wherein the scope holder comprises an open portion configured to allow the passage of the elongate tubular portion of the scope therethrough.

26. The medical device of claim 25 wherein the elongate tubular portion includes a conical portion and the open portion is configured to inhibit passage of at least a portion of the conical portion.

* * * * *